United States Patent [19]

Itakura

[11] Patent Number: 5,555,315
[45] Date of Patent: Sep. 10, 1996

[54] PINHOLE INSPECTION DEVICE AND METHOD

[75] Inventor: Takahiro Itakura, Kariya, Japan

[73] Assignee: Nippondenso Co., Ltd., Kariya, Japan

[21] Appl. No.: 190,514

[22] Filed: Feb. 2, 1994

[30] Foreign Application Priority Data

Feb. 3, 1993 [JP] Japan ................... 5-016611

[51] Int. Cl.$^6$ ............... G06K 9/00; G01N 21/00
[52] U.S. Cl. ............... 382/141; 348/131; 356/239
[58] Field of Search .................. 382/8, 33, 32, 382/30, 141, 144, 212, 209, 217, 218; 348/125, 129, 131; 356/237, 238, 239

[56] References Cited

U.S. PATENT DOCUMENTS

| | | | |
|---|---|---|---|
| 5,047,851 | 9/1991 | Sauerwein et al. | 382/8 |
| 5,166,891 | 11/1992 | Reiter et al. | 382/8 |
| 5,214,712 | 5/1993 | Yamamoto et al. | 382/8 |
| 5,216,485 | 6/1993 | Bird et al. | 382/8 |
| 5,268,968 | 12/1993 | Yoshida | 382/8 |
| 5,287,290 | 2/1994 | Tabara et al. | 382/33 |
| 5,318,173 | 6/1994 | Datari | 382/8 |
| 5,319,720 | 6/1994 | Yokoyama et al. | 382/8 |
| 5,321,772 | 6/1994 | Sawyer | 382/33 |
| 5,347,591 | 9/1994 | Onishi et al. | 382/8 |
| 5,361,307 | 11/1994 | Hartley et al. | 382/8 |

FOREIGN PATENT DOCUMENTS

| | | |
|---|---|---|
| 2191073 | 7/1990 | Japan . |
| 4002952 | 1/1992 | Japan . |

*Primary Examiner*—Joseph Mancuso
*Assistant Examiner*—Gerard Del Rosso
*Attorney, Agent, or Firm*—Cushman, Darby & Cushman

[57] ABSTRACT

An inspection device and method that closely approximates a visual inspection technique for evaluating the quality of a sample. A mask image generation section generates a master image from an image signal of a known good sample. The image signal is used to a first mask image. A plurality of second mask images are generated by magnifying a pattern area of the first mask image by different magnification ratios. A discrimination surface area threshold is set for each mask image. An image under inspection generation section generates a binary image of an unknown sample. A discrimination section takes the logical AND of the binary images of the unknown sample and each mask image, calculates surface areas of pinhole flaws existing in a background area of the binary image under inspection, compares the calculated surface areas and the threshold corresponding to the mask images, and performs a pass/fail judgement of the unknown sample based on the result of this comparison.

16 Claims, 9 Drawing Sheets

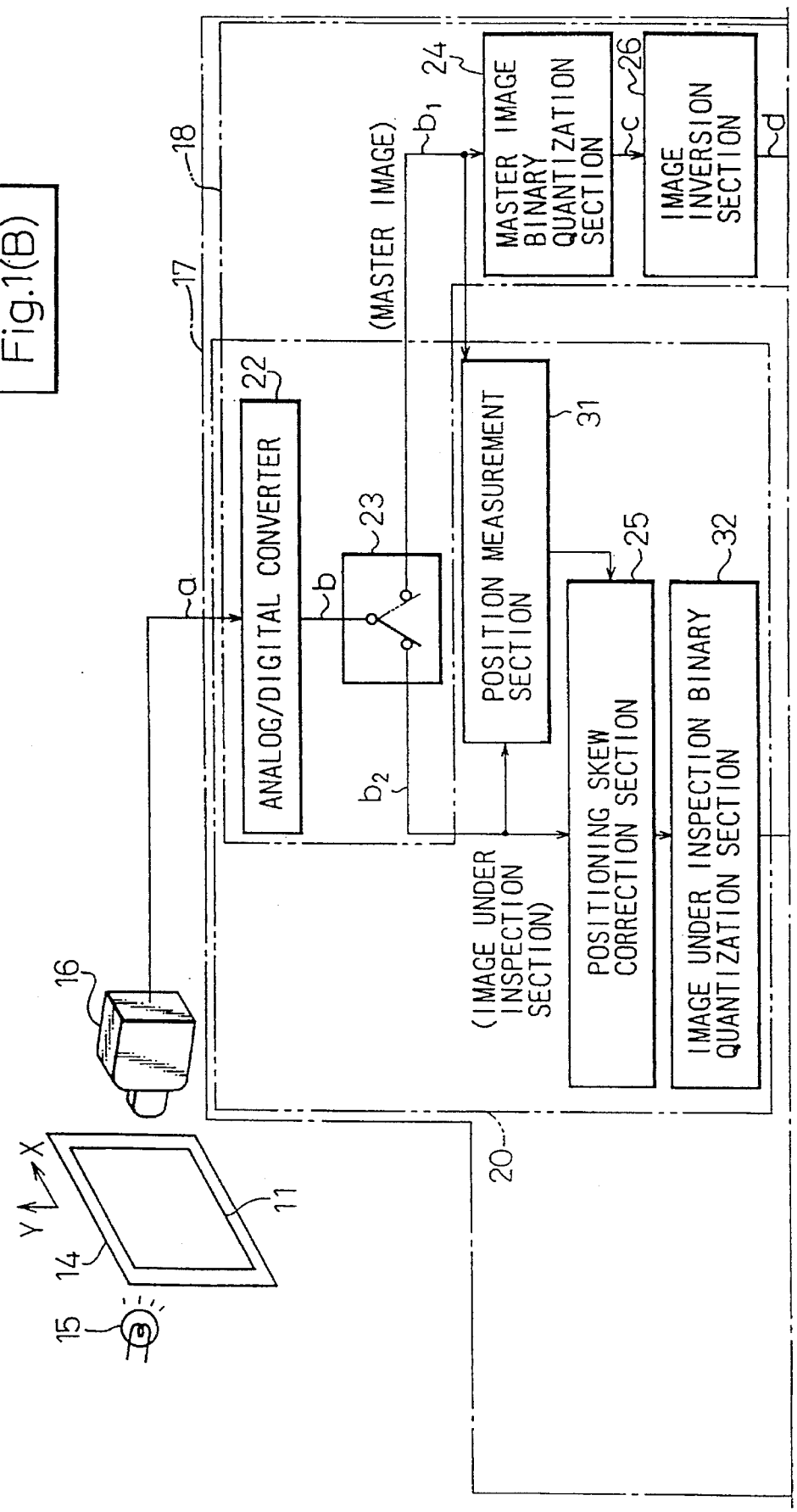

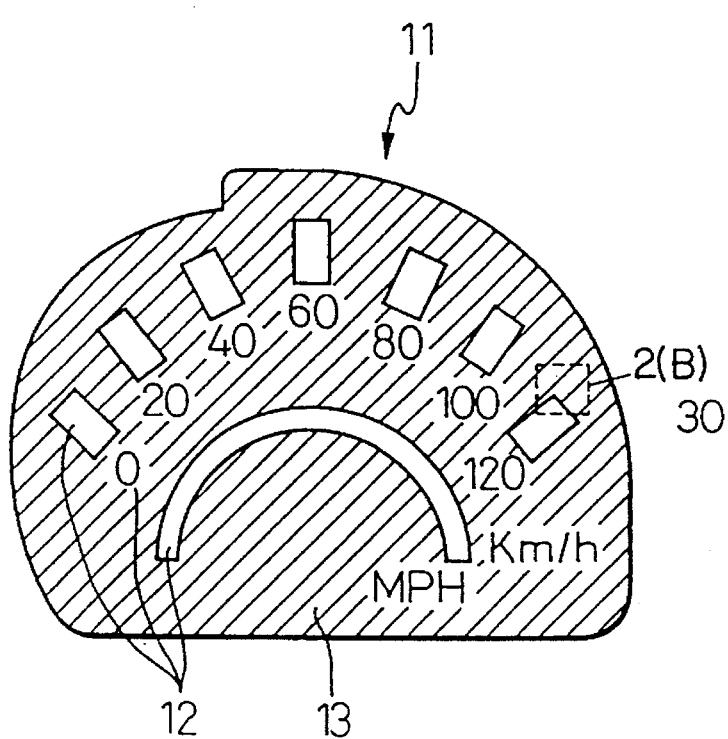
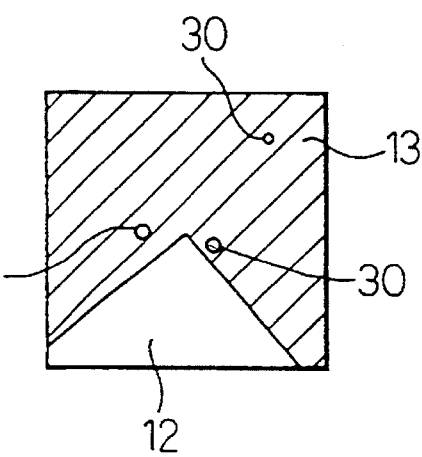
Fig.2(A)
Fig.2(B)

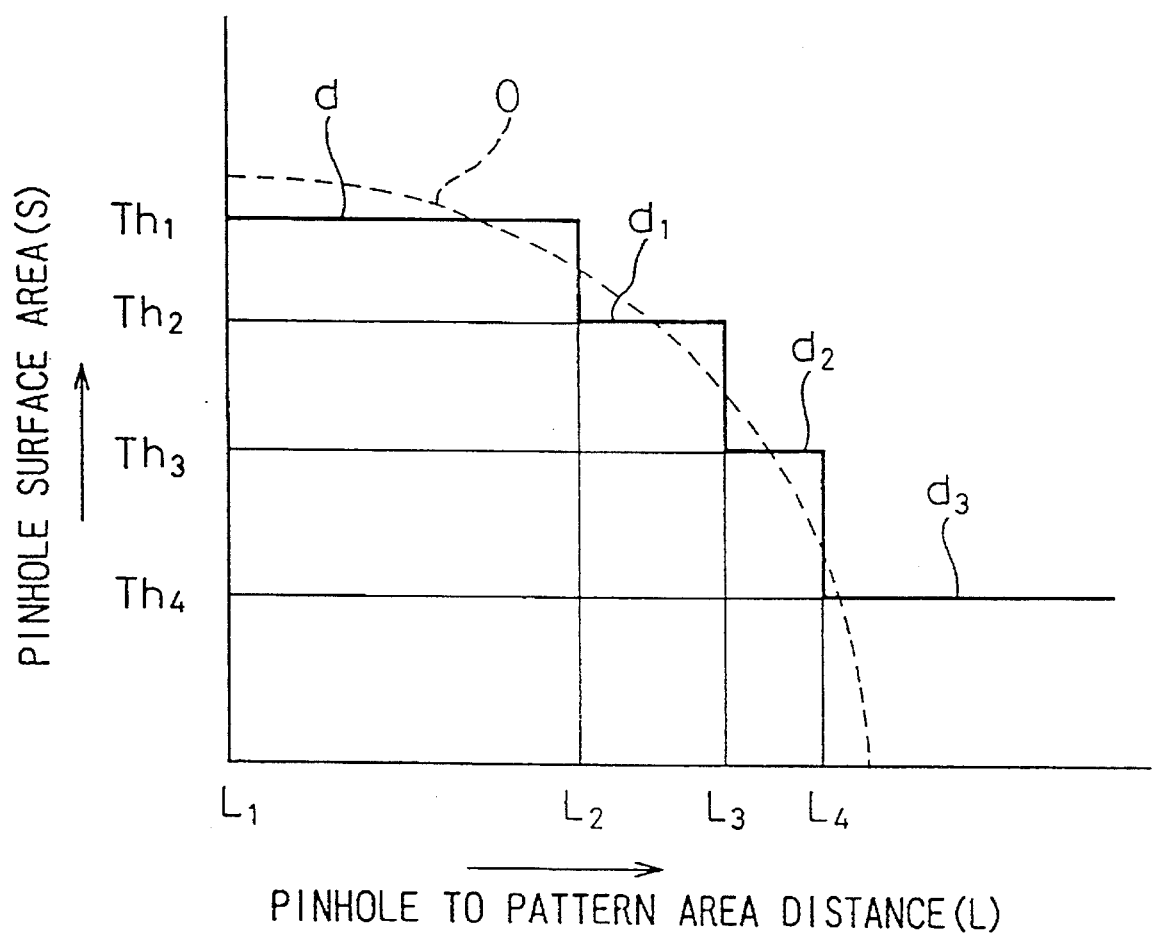

Fig.5(A)
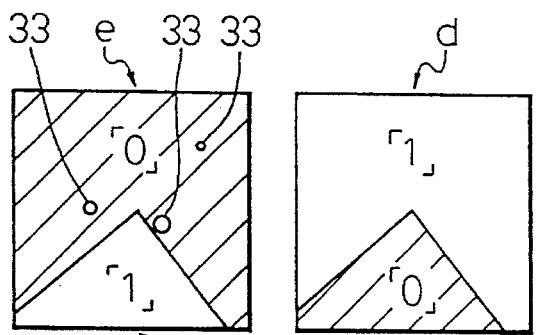
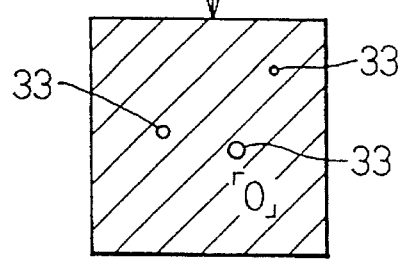
Fig.5(B)
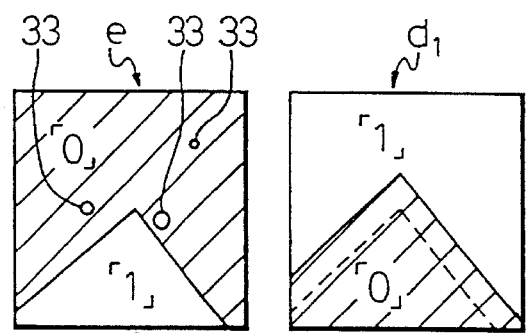
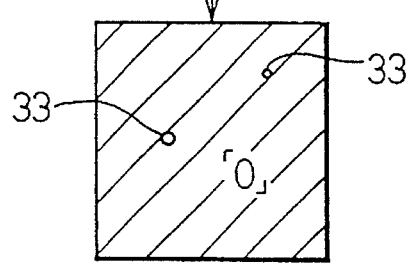
Fig.5(C)
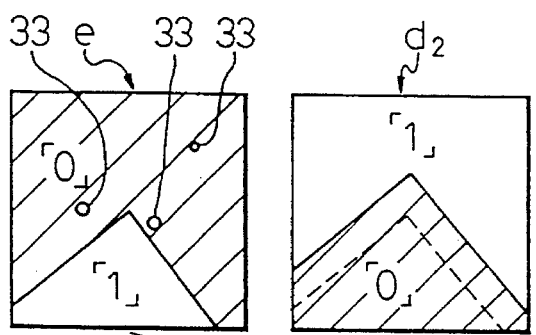
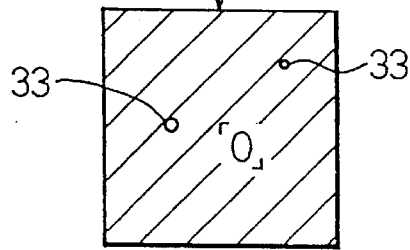
Fig.5(D)
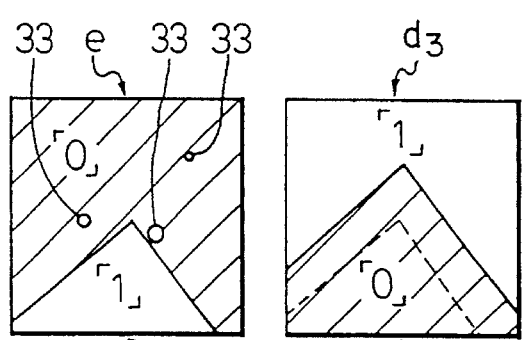
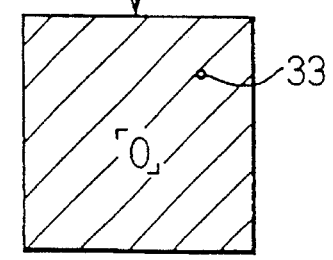

PINHOLE INSPECTION DEVICE AND METHOD

BACKGROUND OF THE INVENTION

1. Field of the Invention

This invention relates to a pinhole inspection device, and, more specifically, to a pinhole inspection device for making a pass/fail quality inspection of a sample under inspection, such as a meter dial plate having a pattern area and a background area, wherein pinholes may exist in the background area.

2. Description of the Related Art

A known pinhole inspection device is disclosed in Japanese Unexamined Patent Publication No. 4-2952.

The above publication discloses a pinhole inspection device that performs a pass/fail discrimination for a sample under Inspection based only on pinhole size.

In a product, such as a meter dial plate, which consist of a pattern area including, for example, numerals, and a background area where no indicia are provided, if there is a pinhole in the background area that is so small that it is not recognized as a pinhole by an observer, the meter dial plate can be properly classified as good. To date, a general visual inspection is considered the best for performing such pass/fail discriminations.

For the reason discussed above, it is desirable that a pinhole inspection device be used to perform pass/fail discrimination for products, such as meter dial plates, wherein the inspection device has a function that approximates a visual pass/fail discrimination as closely as possible.

However, because the pass/fail discrimination by visual inspection and a pass/fail discrimination based on pinhole size have completely different criteria for pass and fail, it is not desirable to use the above-described known pinhole inspection device in a pass/fail discrimination of products, such as meter dial plates.

SUMMARY OF THE INVENTION

The present invention takes the above-stated points into consideration and has as its object to provide a pinhole inspection device which can very closely approximate the pass/fail discrimination made by visual inspection of a product, such as a meter dial plate.

To solve the above-stated problems, the pinhole inspection device of the present invention comprises a holding means which holds the sample under inspection, which includes a pattern area and a background area, wherein the background area capable of including a pinhole; an imaging camera for obtaining an image of the sample under inspection held in the holding means; and a discrimination device, which inputs the image signal from the imaging camera and makes a pass/fail discrimination for the sample under inspection. The discrimination device performs the pass/fail discrimination based on discrimination thresholds, with the surface area of said pinhole and the distance of the pinhole from the background area being varied as parameters.

More specifically, the pinhole inspection device of the present invention comprises a sample placement means which holds the sample under inspection. The sample consists of a pattern area and a background area, wherein the background area could contain a pinhole. An imaging camera obtains an image of the sample under inspection held by the sample placement means. A discrimination device makes a pass/fail discrimination of the sample under inspection. The discrimination device uses the surface area of the pinhole and the distance of the pinhole from the pattern area as discrimination criteria, and a pass/fail discrimination is performed according to basic discrimination criteria established in accordance with visual inspection.

The reason the present invention uses the surface area of the pinhole and the distance of the pinhole from the pattern area as criteria in making a pass/fail discrimination of the sample under inspection is based on the considerations described below.

Essentially, if a pinhole exists in proximity to the pattern area of a product, such as meter dial plate, even if the pinhole is relatively large, the illumination light passing through this pinhole provides almost no visual stimulus to the observer (driver). However, if a pinhole exists at a distance from the pattern area, even if the pinhole is relative small, the light passing through it provides visual stimulus, resulting in a marring of the appearance of the products. Thus, in a pass/fail discrimination of a designed product such as meter dial plate, it is preferable to use the visual characteristics of such designed product, as described above, as a discrimination criteria.

It is therefore possible in the present invention to very closely approximate the pass/fail discrimination of designed products, such as meter dial plates, as would be done using a visual inspection.

BRIEF DESCRIPTION OF THE DRAWINGS

FIGS. 1, 1(A) and 1(B) show the overall configurations of the first embodiment of the pinhole inspection device;

FIGS. 2(A) and 2(B) show the structure of a meter dial plate;

FIG. 4 is a graph for explaining the discrimination surface area threshold;

FIG. 5(A), 5(B), 5(C), and 5(D) illustrate operations of the first to fourth masks;

DETAILED DESCRIPTION OF THE PREFERRED EMBODIMENTS

The configuration and operation of the first embodiment of the present invention are described below with reference to FIGS. 1–5.

1. Configuration

Figure 1B:
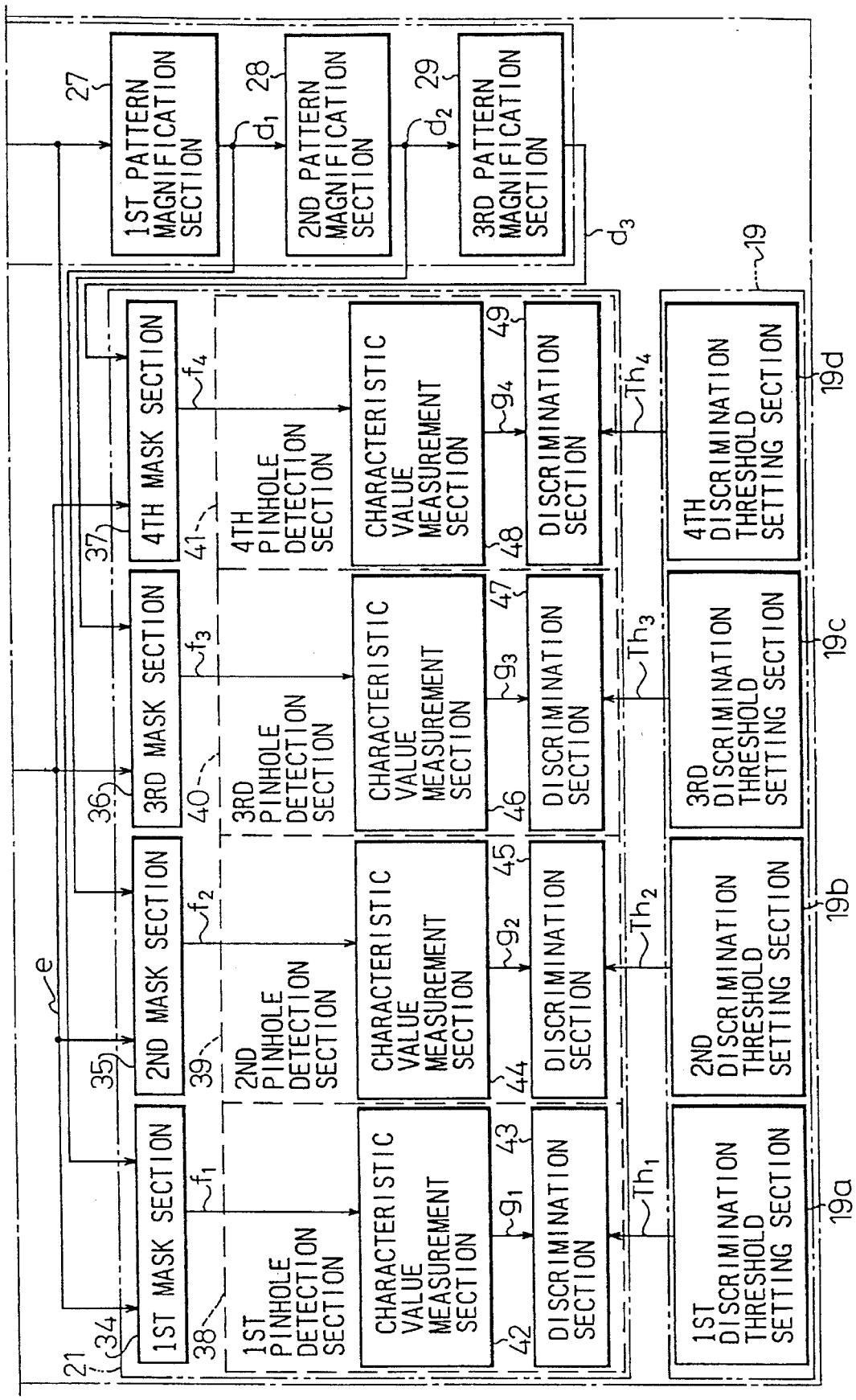

FIGS. 1(A) and 1(B) show the configuration of the pinhole inspection device, wherein the sample under inspection is a meter dial plate.

In FIG. 1(A), numeral 11 identifies the meter dial plate as the sample under inspection. Meter dial plate 11 consists of pattern area 12, which consists of elements such as numerals, and a background area 13 (refer to FIG. 2). The meter dial plate is set onto X-Y table 14, which functions as a holding means, and receives illumination from its rear by means of an illumination means 15. An imaging camera 16 is located at the front side of meter dial plate 11. Imaging camera 16 sequentially scans the inspection area of meter dial plate 11 as X-Y table 14 moves, enabling it to form images of the entire surface of meter dial plate 11. Alternatively, instead of the above type of moving holding means 14, it is possible to use a fixed holding means to hold meter dial plate 11 in a fixed position, and to use a robot, for example, to move imaging camera 16 to obtain images of meter dial plate 11.

In FIGS. 1(A) and 1(B), numeral 17 identifies the discrimination device. Discrimination device 17 consists of mask image generation section 18, discrimination threshold setting sections 19, image under inspection generation section 20, and discrimination section 21.

i) Mask Image Generation Section 18

Mask image generation section 18 has an analog/digital converter 22 which is connected to the output of imaging camera 16. Analog/digital converter 22 converts an analog image signal a of the sample under inspection which is output from imaging camera 16 into a digital signal b, which is a dark/light graded image. Analog/digital converter 22 is a constituent element of image under inspection generation section 20.

The output of analog/digital converter 22 is connected to selector switch 23. Selector switch 23 is set up so that when operating the mask image generation section 18, it is set to electrically connect the analog/digital converter 22 and the master image binary quantization section 24, and when operating the image under inspection generation section 20, it is set to electrically connect analog/digital converter 22 to positioning skew correction section 25. Therefore, selector switch 23 is a constituent element of image under inspection generation section 20.

Selector switch 23 has connected to it a master image binary quantization section 24. With a known good meter dial plate 11 as the sample under inspection (in the strict sense this is not the sample under inspection, but for the present invention a good meter dial plate is taken as being included in the meaning of sample under test) mounted onto X-Y table 14, the good meter dial plate is imaged by imaging camera 16 to obtain a dark/light graded image (master image) b1, which is compared by master image binary quantization section 24 using a prescribed threshold value, pattern area 12 being binarily quantized to a logic value of 1, and background area 13 being binarily quantized to a Logic value of 0, thereby generating the binarily quantized master image c.

The output of the master image binary quantization section 24 has connected to it the image inversion section 26. This image inversion section 26 is configured so as to invert the binarily quantized master image generated by master image binary quantization section 24, inverting the logic value 1 of the pattern area 12 to logic 0, and inverting the logic value 0 of the background area 13 to logic 1, resulting in the generation of the inverted binarily quantized master image, which is the 1st mask image d (refer to FIG. 3(A)).

The output of image inversion section 26 has connected to it the 1st pattern magnification section 27. This 1st pattern magnification section 27 is configured so as to magnify the pattern area 12 of the inverted binarily quantized master image d generated by image inversion section 26 by a prescribed magnification ratio of $\alpha$, resulting in the generation of an inverted binarily quantized master image $d_1$ which has a magnified pattern area 12a (refer to FIG. 3(B)). The inverted binarily quantized master image $d_1$, which has magnified pattern area 12a, is one of the plurality of 2nd mask images in the present invention.

The output of 1st pattern magnification section 27 has connected to it the 2nd pattern magnification section 28. This 2nd pattern magnification section 28 is configured so as to magnify the magnified pattern area 12a of the inverted binarily quantized master image $d_1$ generated by image inversion section 27 and having a magnified pattern area 12a by a prescribed magnification ratio of $\beta$, resulting in generation of an inverted binarily quantized master image $d_2$ which has a further magnified pattern area 12b (refer to FIG. 3(C)). The inverted binarily quantized master image $d_2$, which has magnified pattern area 12b, is another of the plurality of 2nd mask images in the present invention.

The output of 2nd pattern magnification section 28 has connected to it the 3rd pattern magnification section 29. This 3rd pattern magnification section 29 is configured so as to magnify the magnified pattern area 12a of the inverted binarily quantized master image $d_2$ generated by image inversion section 28 and having a magnified pattern area 12b by a prescribed magnification ratio of $\gamma$, resulting in the generation of an inverted binarily quantized master image $d_3$ which has a further magnified pattern area 12b (refer to FIG. 3(D)). The inverted binarily quantized master image $d_3$, which has magnified pattern area 12c, is the last of the plurality of 2nd mask images in the present invention.

Figure 3A:
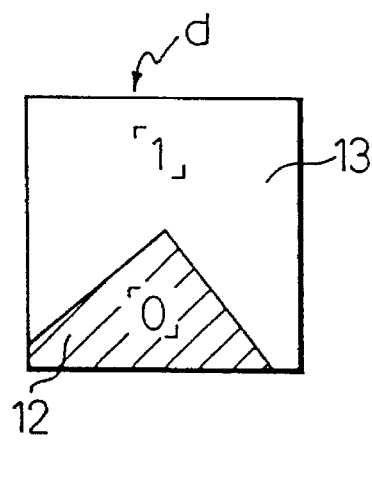
FIG. 3(A), 3(B), 3(C), and 3(D) show the reference mask and correction mask images.
Figure 3B:
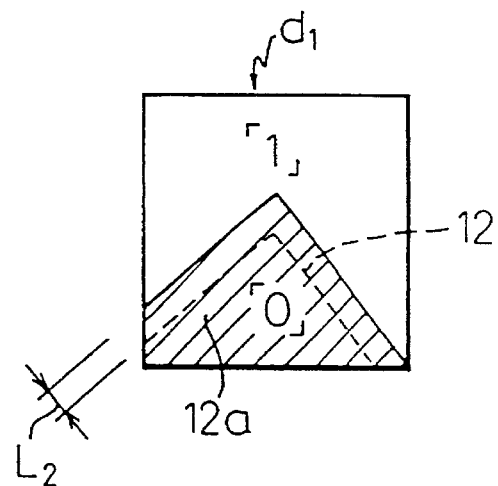
Figure 3C:
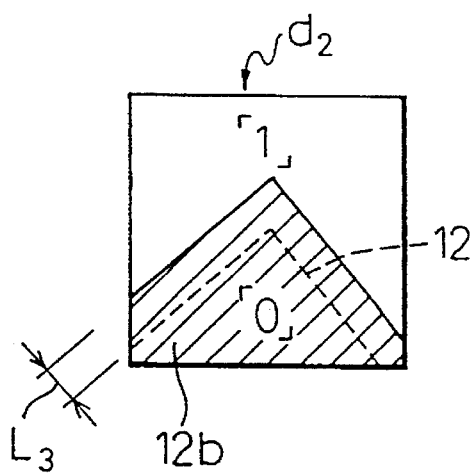
Figure 3D:
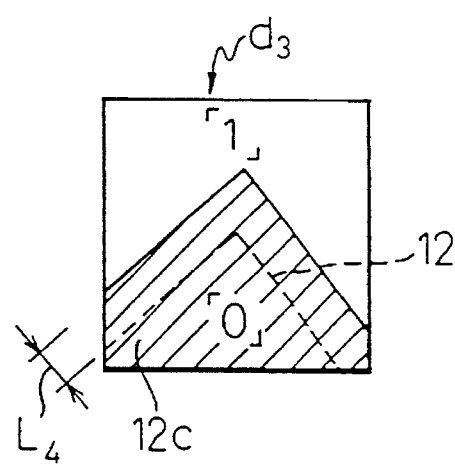

As explained above, mask image generation section 18 generates the 1st mask image d (FIG. 3(A)) by performing binary quantization and image inversion of master image b1, and then generates mask images $d_1$, $d_2$, and $d_3$ (FIG. 3(B), 3(C), and 3(D)) by magnifying pattern area 12 of said mask image d by mutually differing magnification ratios $\alpha$, $\alpha \cdot \beta$, and $\alpha \cdot \beta \cdot \gamma$.

ii) Discrimination Threshold Setting Sections 19

Discrimination threshold setting sections 19 are configured so as to set the pinhole surface areas (discrimination surface area thresholds) to be used as the discrimination thresholds for the above-stated 1st and 2nd mask images, d, $d_1$, $d_2$, and $d_3$.

As shown in FIG. 4, the above-stated discrimination surface area thresholds are set as $Th_1$ for 1st mask image d, as $Th_2$ for 2nd mask image $d_1$, as $Th_3$ for 2nd mask image $d_2$, and as $Th_4$ for 2nd image mask $d_3$. Stated differently, the discrimination surface area threshold is set as $Th_1$ when the pinhole to pattern area distance L is between $L_1$ (=0) and $L_2$ (refer to FIG. 3(B)), is set to $Th_2$ when the pinhole to pattern area distance L is between $L_2$ and $L_3$ (Refer to FIG. 3(C)), is set the $Th_3$ when the pinhole to pattern area distance L is between $L_3$ and $L_4$ (Refer to FIG. 3(D)), and is set to $Th_4$ when the pinhole to pattern area distance L is $L_4$ or greater.

The reason for varying the discrimination surface area threshold with respect to changes in the pinhole to pattern area distance L is that for a designed product, such as meter dial plate 11, if pinhole 30 exists close to pattern area 12 (refer to FIG. 2) and even if pinhole 30 is relatively large, the illumination light passing through this pinhole 30 provides almost no visual stimulus to the observer (driver). However, if pinhole 30 exists at a distance relatively far from pattern area 12 and even if the pinhole is relatively small, the light passing through it provides visual stimulus to the observer, resulting in a marring of the appearance of the products, such as meter dial plates. So that in pass/fail discrimination of such products, it was noticed that a visual inspection is preferably used, with the visual characteristics of such designed products, as described above, being used as discrimination thresholds. This embodiment of the pinhole inspection device uses an approximation of the basic visual inspection criterion O (refer to FIG. 4). The above-stated discrimination thresholds also agrees with Weber's Law.

Thus, the discrimination surface area threshold $Th_1$ for 1st mask image d is set at discrimination threshold setting section 19a, the discrimination surface area threshold $Th_2$ for 2nd mask image $d_1$ is set at discrimination threshold setting section 19b, the discrimination surface area threshold $Th_3$ for 2nd mask image $d_2$ is set at discrimination threshold setting section 19c, and the discrimination surface area threshold $Th_3$ for 2nd mask image $d_3$ is set at discrimination threshold setting section 19d.

iii) Image Under Inspection Generation Section 20

The image under inspection generation section 20 comprises analog/digital converter 22, position measurement section 31, positioning skew correction section 25, and image under inspection binary quantization section 32, and when the meter dial plate 11, which is the sample under inspection in the strict sense, is mounted on X-Y table 14 and the meter dial plate 11 is imaged by imaging camera 16, the image under inspection generation section 20 is placed in operating condition by selector switch 23.

Analog/digital converter 22 is configured to convert the analog image signal a of the meter dial plate 11, which is the sample under inspection in the strict sense, to a digital dark/light graded image b.

Position measurement section 31 and positioning skew correction section 25 are configured so as to correct the positioning skew which occurs between master image $b_1$ and image under inspection $b_2$ (the dark/light graded image of the sample under inspection in the strict sense) due at least in part to the difference in the way in which the good sample under inspection meter dial plate and meter dial plate 11 in the strict sense are mounted onto X-Y table 14, thereby achieving positioning alignment between $b_1$ and $b_2$.

Image under inspection binary quantization section 32 is configured to compare image under inspection $b_2$, which was positioned corrected by the above position measurement section 31 and positioning skew correction section 25, with a prescribed threshold value, generating a binarily quantized image under inspection e by quantizing the pattern area 12 (bright area) to a logic 1 and the background area 13 (dark area) to a logic 0. Therefore, if there exists a pinhole 30 in the background area 13 of meter dial plate 11 in the strict sense, the pinhole 30 becomes a bright area, so that pinhole 33 in the binarily quantized image under inspection 33 is at logic 1.

In this manner, image under inspection generation section 20 generates a position-corrected binarily quantized image under inspection e from image signal a of the sample under inspection 11 in the strict sense.

iv) Discrimination Section 21

Discrimination section 21 consists of 1st, 2nd, 3rd, and 4th mask sections 34, 35, 36, and 37, and 1st, 2nd, 3rd, and 4th pinhole detection sections 38, 39, 40, and 41.

The 1st mask section 34 is connected to the outputs of image inversion section 26 and image under inspection binary quantization section 32, and is configured so as to take the logical product (AND) of the inverted binarily quantized master image (1st mask image) d and the binarily quantized image under inspection e. Because in the 1st mask image d, as described above, the pattern area 12 is logic 0 and the background area 13 is logic 1, and in the binarily quantized image under inspection e, the pattern area 12 is logic 1 and the background area 13 is logic 0, in only the case in which there exists a pinhole part 33 in the background area 13 of the binarily quantized image under inspection, the effect of taking the logical AND of these two images is that the pixels including pinhole part 33 are output as logic 1 (refer to FIG. 5(A)). The resulting pinhole part data $f_1$ is input to the characteristic value measurement section 42 of 1st pinhole detection section 38.

The 2nd mask section 35 is connected to the outputs of 1st pattern magnification section 27 and image under inspection binary quantization section 32, and is configured so as to take the logical AND of the 2nd mask image $d_1$ and the binarily quantized image under inspection e. Because in the 2nd mask image $d_1$, as described above, the magnified pattern area 12a is logic 0 and the background area 13 is logic 1, and in the binarily quantized image under inspection e, the pattern area 12 is logic 1 and the background area 13 is logic 0, the result of taking the logical AND of these two images is that, of background area 13 of the binarily quantized image under inspection e, only the pinhole part 33 existing in the part that does not overlap with the magnified pattern area 12a is output as logic 1 (refer to FIG. 5(B)). The resulting pinhole part data $f_2$ is input to the characteristic value measurement section 44 of 2nd pinhole detection section 39.

The 3rd mask section 36 is connected to the outputs of 2nd pattern magnification section 28 and image under inspection binary quantization section 32, and is configured so as to take the logical AND of the 2nd mask image $d_2$ and the binarily quantized image under inspection e. Because in the 2nd mask image $d_2$, as described above, the magnified pattern area 12b is logic 0 and the background area 13 is logic 1, and in the binarily quantized image under inspection e, the pattern area 12 is logic 1 and the background area 13 is logic 0, the result of taking the logical AND of these two images is that, of background area 13 of the binarily quantized image under inspection e, only the pinhole part 33 existing in the part that does not overlap with the magnified pattern area 12b is output as logic 1 (refer to FIG. 5(C)). The resulting pinhole part data $f_3$ is input to the characteristic value measurement section 46 of 3rd pinhole detection section 40.

The 4th mask section 37 is connected to the outputs of 3rd pattern magnification section 29 and image under inspection binary quantization section 32, and is configured so as to take the logical AND of the 2nd mask image $d_3$ and the binarily quantized image under inspection e. Because in the 2nd mask image $d_3$, as described above, the magnified pattern area 12c is logic 0 and the background area 13 is logic 1, and in the binarily quantized image under inspection e, the pattern area 12 is logic 1 and the background area 13 is logic 0, the result of taking the logical AND of these two images is that, of background area 13 of the binarily quantized image under inspection e, only the pinhole part 33 existing in the part that does not overlap with the magnified pattern area 12c is output as logic 1 (refer to FIG. 5(D)). The resulting pinhole part data $f_4$ is input to the characteristic value measurement section 48 of 4th pinhole detection section 41.

The 1st pinhole detection section 38 consists of characteristic value measurement section 42 and discrimination section 43. The characteristic value measurement section 42 is configured so as to calculate the surface area $S_i$ of each pinhole i (where i=1 to n) based on pinhole data $f_1$, and output this characteristic value data $g_1$ to discrimination section 43. In performing the calculations of these surface areas $S_i$, it is possible, for example, to count the number of pixels in the aggregate of pixels which have a value logic 1, which represents pinholes i. Discrimination section 43 performs a comparison of the magnitude each of the pinhole surface areas $S_i$ indicated by characteristic values $g_1$ and the discrimination surface area criterion $Th_1$ which is set by second the discrimination threshold setting section 19a. If any pinhole surface area Si is larger than the discrimination surface area criterion $Th_1$, the meter dial plate 11 is judged to be failed.

The 2nd pinhole detection section 39, similar to the above-stated 1st pinhole detection section 38, consists of characteristic value measurement section 44 and discrimination section 45. The characteristic value measurement section 44 is configured so as to calculate the surface are Si of each pinhole i (excluding those pinhole parts 33 that overlap with the magnified pattern area 12a) based on pinhole data $f_2$, and output this characteristic value data $g_2$ to discrimination section 45. The method of calculating the surface areas Si is similar to that for characteristic value measurement section 42, which is described above. Discrimination section 45 performs a comparison of the magnitude each of the pinhole surface areas Si indicated by characteristic values $g_2$ and the discrimination surface area criterion $Th_2$ which is set by second the discrimination threshold setting section 19b. If any pinhole surface area Si is larger than the discrimination surface area criterion $Th_2$, the meter dial plate 11 is judged to be failed.

The 3rd pinhole detection section 40, similar to the above-stated 1st pinhole detection section 38, consists of characteristic value measurement section 46 and discrimination section 47. The characteristic value measurement section 46 is configured so as to calculate the surface area Si of each pinhole i (excluding those pinhole parts 33 that overlap with the magnified pattern area 12b) based on pinhole data $f_3$, and output this characteristic value data g3 to discrimination section 47. The method of calculating the surface areas Si is similar to that for characteristic value measurement section 42, which is described above. Discrimination section 47 performs a comparison of the magnitude each of the pinhole surface areas Si indicated by characteristic values g3 and the discrimination surface area criterion $Th_3$ which is set by the third discrimination threshold setting section 19c. If any pinhole surface area Si is larger than the discrimination surface area criterion $Th_3$, the meter dial plate 11 is judged to be failed.

The 4th pinhole detection section 41, similar to the above-stated 1st pinhole detection section 38, consists of characteristic value measurement section 48 and discrimination section 49. The characteristic value measurement section 48 is configured so as to calculate the surface area Si of each pinhole i (excluding those pinhole parts 33 that overlap with the magnified pattern area 12c) based on pinhole data $f_4$, and output this characteristic value data $g_3$ to discrimination section 49. The method of calculating the surface areas Si is similar to that for characteristic value measurement section 42, which is described above. Discrimination section 49 performs a comparison of the magnitude each of the pinhole surface areas Si indicated by characteristic values $g_4$ and the discrimination surface area criterion $Th_4$ which is set by the forth discrimination threshold setting section 19d. If any pinhole surface area Si is larger than the discrimination surface area criterion $Th_4$, the meter dial plate 11 is judged to be failed.

In this manner, discrimination section 21 is configured so as to take the logical AND of the binarily quantized images under inspection d, $d_1$, $d_2$, and $d_3$, calculate the surface areas Si of the pinholes in the part of background area 13 which does not overlap with magnified pattern areas 12a, 12b, 12c, and 12d, perform a magnitude comparison of said calculated surface areas Si with the discrimination surface areas $Th_1$, $Th_2$, $Th_3$, and $Th_4$, which are used as discrimination thresholds corresponding to said masks d, $d_1$, $d_2$, and $d_3$, and if a calculated surface area Si is larger than the corresponding discrimination surface area threshold $Th_1$, $Th_2$, $Th_3$, and $Th_4$, judge said meter dial plate 11 to be failed.

2. Operation

The following is a description of the operation of pinhole inspection device configured as described above. As described below, the operation of the pinhole inspection device can be divided in terms of time series into mask image generation processing and pass/fail discrimination processing each of which is discussed in turn below.

i) Mask Image Generation Processing

A meter dial plate 11 to be used as the known good sample is mounted on X-Y table 14, and illuminated from the rear by illumination means 15. The X-Y table 14 is then moved appropriately, and imaging camera 16 is used to sequentially scan the area of meter dial plate 11 to be inspected, resulting in image signal a being output to discrimination device 17.

At discrimination device 17, analog/digital converter 22 converts image signal a to a digital signal, which is a graded dark/light graded image. This dark/light graded image is input by selector switch 23 as master image $b_1$ both to position measurement section 31 and to master image binary quantization section 24.

Position measurement section 31 measures the position of master image $b_1$, and generates the data for skew correction, which is performed by positioning skew correction section 25.

Master image binary quantization section 24 performs a binary quantization of said master image $b_1$, outputting binarily quantized master image c to image inversion section 26. At this point, in the binarily quantized master image e, the pattern area 12 has been set to logic 1, and the background area 13 has been set to logic 0.

At image inversion section 26, binarily quantized master image c is inverted, the logic 1 of pattern area 12 being inverted to logic 0, and the logic 0 of background area 13 being inverted to logic 1, thereby creating the inverted binarily quantized master image (1st mask image) d (FIG. 3 (A)).

The 1st master image d is input to 1st pattern magnification section 27, this 1st pattern magnification section 27 magnifying the pattern area 12 by a prescribed magnification ratio $\alpha$, resulting in generation of an inverted binarily quantized master image (2nd mask image) $d_1$ which has a magnified pattern area 12a (FIG. 3(B)).

The 2nd master image $d_1$ is input to 2nd pattern magnification section 28, this 2nd pattern magnification section 28 magnifying pattern area 12 by a prescribed magnification ratio $\alpha \cdot \beta$, resulting in generation of an inverted binarily quantized master image (2nd mask image) $d_2$, with a magnified pattern area 12b (FIG. 3(C)).

The 2nd master image $d_2$, is input to 2nd pattern magnification section 29, this 2nd pattern magnification section 29 magnifying pattern area 12 by a prescribed magnification ratio $\alpha \cdot \beta \cdot \gamma$, resulting in generation of an inverted binarily quantized master image (2nd mask image) $d_3$ with a magnified pattern area 12 (FIG. 3(D))

Mask image generation as described above only needs to be done once by reading in a know good sample at the beginning of inspection.

Also, in the present invention, the correction mask image, which is generated with respect to the 1st mask image, can include not only magnification, but reduction as well, the number of types is not limited to the three types stated in the particular example above, but rather the desired number of types is selectable.

ii) Pass/Fail Discrimination Processing

A meter dial plate 11 to serve as the sample under inspection in the strict sense is mounted on X-Y table 14, and illuminated from the rear by illumination means 15. The X-Y table 14 is then moved appropriately, and imaging camera 16 is used to sequentially scan the area of meter dial plate 11 to be inspected, resulting in image signal a being output to discrimination device 17.

At discrimination device 17, analog/digital converter 22 converts image signal a to a digital signal, which is a graded dark/light graded image. This dark/light graded image is input by selector switch 23 as image under inspection $b_2$ both to position measurement section 31 and to positioning skew correction section 25.

Position measurement section 31 measures the position of image under inspection $b_2$, detects the direction and amount of the positioning skew between image under inspection $b_2$ and master image $b_1$, and outputs this data related to positioning skew to positioning skew correction section 25.

Positioning skew correction section 25 aligns the position of image under inspection $b_2$ with master image $b_1$ based on data related to positioning skew from position measurement section 31, and after this alignment, outputs image under inspection $b_2$ to image under inspection binary quantization section 32.

Image under inspection binary quantization section 32 performs binary quantization on the image under inspection $b_2$, which has been position aligned, and outputs the binarily quantized image under inspection e to the 1st through 4th mask sections 34, 35, 36, and 37. At this point, in the binarily quantized image under inspection e, the pattern area 12 has been set to logic 1, and the background area 13 has been set to logic 0. If a pinhole exists in background area 13 of the sample under inspection 11, the pinhole area 33 of binarily quantized image under inspection e is set to logic 1, because in the same manner as the pattern area 12, illumination light passes through it.

The 1st mask section 34 takes the logical AND of the binarily quantized image under inspection end the mask image d, and in only the case in which there exists a pinhole i part in the background area 13 of the binarily quantized image under inspection e, the pixels for said pinhole i are set to logic 1, the pinhole part data $f_1$ being output to characteristic value measurement section 42 (FIG. 5 (A)).

The 2nd mask section 35 takes the logical AND of the binarily quantized image under inspection e and the mask image $d_1$, and of the background area 13 of the binarily quantized image under inspection e, only the pixels for a pinhole i which does not overlap the magnified pattern area 12a are set to logic 1, the pinhole part data $f_2$ being output to characteristic value measurement section 44 (FIG. 5(B)).

The 3rd mask section 36 takes the logical AND of the binarily quantized image under inspection e and the mask image $d_2$, and of the background area 13 of the binarily quantized image under inspection e, only the pixels for a pinhole i which does not overlap the magnified pattern area 12b are set to logic 1, the pinhole part data $f_3$ being output to characteristic value measurement section 46 (FIG. 5(C)).

The 4th mask section 37 takes the logical AND of the binarily quantized image under inspection e and the mask image $d_3$, and of the background area 13 of the binarily quantized image under inspection e, only the pixels for a pinhole i which does not overlap the magnified pattern area 12c are set to logic 1, the pinhole part data $f_4$ being output to characteristic value measurement section 48 (FIG. 5 (D)).

Characteristic value measurement section 42 calculates each surface area Si for the pinhole parts i extracted using 1st mask section 34 by counting the number of logic 1 pixels in each of the aggregates of pixels, and outputs the characteristic value data $g_1$, which indicates the calculated surface area Si, to discrimination section 43. Discrimination section 43 performs a magnitude comparison of each surface area Si, which is indicated by characteristic value data $g_1$, with the discrimination surface area threshold Th1, and if any pinhole surface area Si is larger than the discrimination surface area threshold $Th_1$, meter dial plate 11 is judged to be failed.

Characteristic value measurement section 44 calculates each surface area Si for the pinhole parts i extracted using 1st mask section 35 by counting the number of logic 1 pixels in each of the aggregates of pixels, and outputs the characteristic value data $g_2$ which indicates the calculated surface area Si to discrimination section 45. Discrimination section 45 performs a magnitude comparison of each surface area Si, which is indicated by characteristic value data $g_2$, with the discrimination surface area threshold $Th_2$, and if any pinhole surface area Si is larger than the discrimination surface area threshold $Th_2$, meter dial plate 11 is judged to be failed.

Characteristic value measurement section 46 calculates each surface area Si for the pinhole parts i extracted using 1st mask section 36 by mounting the number of logic 1 pixels in each of the aggregates of pixels, and outputs the characteristic value data $g_3$ which indicates the calculated surface area Si to discrimination section 47. Discrimination section 47 performs a magnitude comparison of each surface area Si, which is indicated by characteristic value data $g_3$, with the discrimination surface area threshold Th3, and if any pinhole surface area Si is larger than the discrimination surface area threshold $Th_3$, meter dial plate 11 is judged to be failed.

Characteristic value measurement section 48 calculates each surface area Si for the pinhole parts i extracted using 1st mask section 37 by counting the number of logic 1 pixels in each of the aggregates of pixels, and outputs the characteristic value data $g_4$ which indicates the calculated surface area Si to discrimination section 49. Discrimination section 49 performs a magnitude comparison of each surface area Si, which is indicated by characteristic value data $g_3$, with the discrimination surface area threshold $Th_4$, and if any pinhole surface area Si is larger than the discrimination surface area threshold $Th_4$, meter dial plate 11 is judged to be failed.

As described above, the discrimination device 17 in the pinhole inspection device related to the 1st embodiment, in addition to generating the 1st mask image d from the image signal a of the sample under inspection 11 by performing binary quantization of master image $b_1$, is configured so as to comprise a mask image generation section 18 which magnifies the pattern area 12 of 1st mask image d by mutually differing magnification ratios $\alpha$, $\alpha \cdot \beta$, and $\alpha \cdot \beta \cdot \gamma$, thus creating a plurality of 2nd mask images d, $d_1$, and $d_2$; a discrimination threshold setting section 19, which sets the discrimination surface areas $Th_1$, $Th_2$, $Th_3$, and $Th_4$ which are used as discrimination thresholds corresponding to each of the mask images d, $d_1$, $d_2$, and $d_3$; an image under inspection generation section 20, which generates a binarily quantized image under inspection from the image signal a of the sample under inspection; and discrimination section 21 which takes a logical AND of the binarily quantized image under inspection with each of the mask images d, $d_1$, $d_2$, and $d_3$, and which calculates the surface areas of the Si for each of the pinholes which exist in background area 13 which do not overlap with pattern area 12 or magnified pattern areas 12a, 12b, or 12c, making a magnitude comparison between calculated surface areas Si and the discrimination surface area thresholds $Th_1$, $Th_2$, $Th_3$, and $Th_4$ which correspond to mask images d, $d_1$, $d_2$, and $d_3$, and judges a sample under inspection to be bad if a calculated surface area Si is larger than the discrimination surface area thresholds $Th_1$, $Th_2$, $Th_3$, or $Th_4$.

The above-stated discrimination surface area thresholds $Th_1$, $Th_2$, $Th_3$, or $Th_4$ are established based on the magnification ratios of each of the masks d, $d_1$, $d_2$, and $d_3$, or stated differently, on the distance between the pinhole and the pattern area, so that this is based on the visual inspection discrimination criterion 0.

For this reason, using this embodiment of the pinhole inspection device, it is possible to perform pass/fail discrimination which extremely closely approximates a visual inspection.

In the above-described embodiment, while four masks, d, $d_1$, $d_2$, and $d_3$, are used, it is also possible to use a different number of masks, depending on the speed of response off discrimination device 17.

The configuration and then the operation of the second embodiment of the pinhole inspection device are described below, with reference made to FIG. 6 through FIG. 9.

1. Configuration

Figure 6:
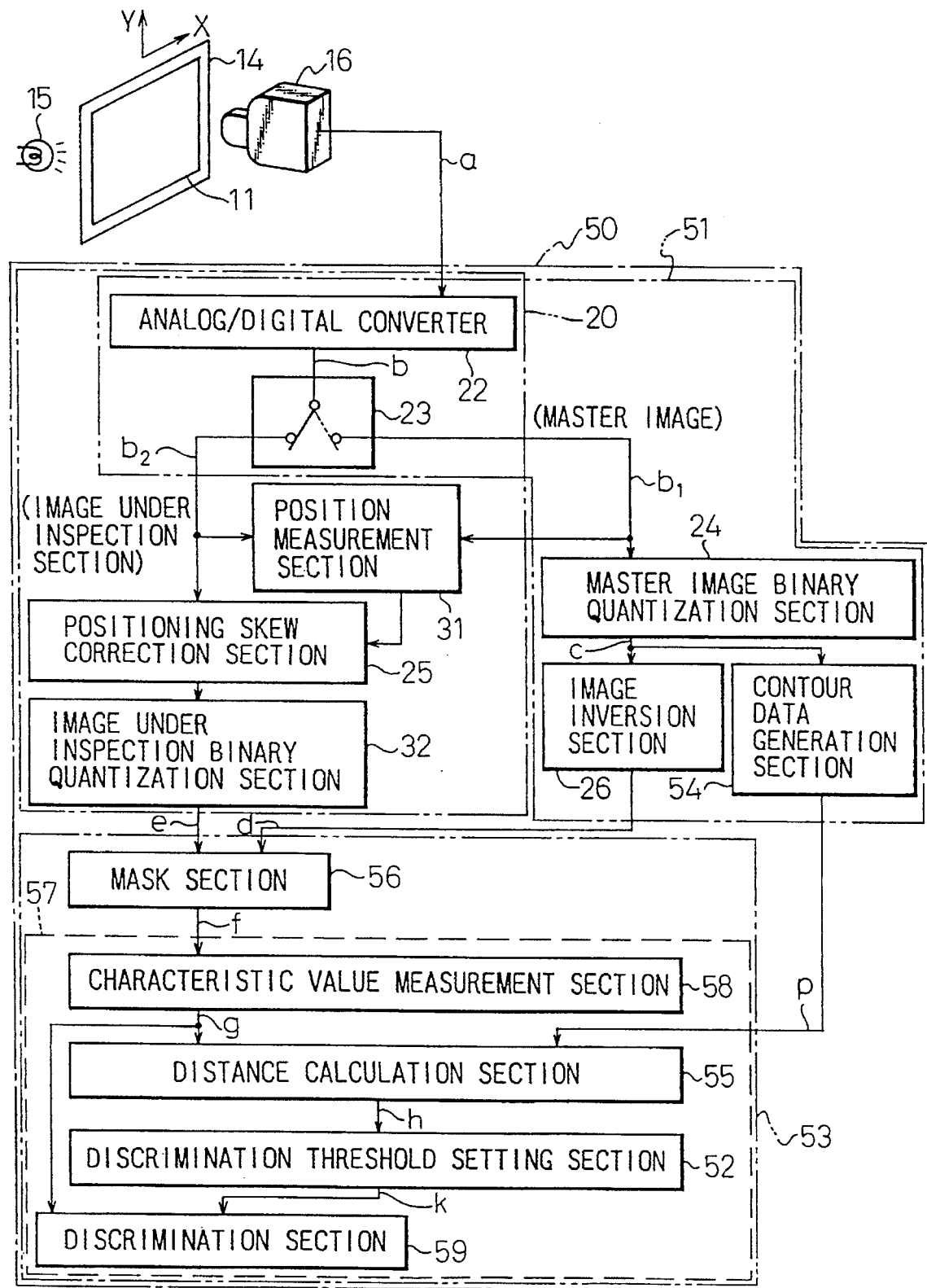
FIG. 6 shows the overall configuration of a second embodiment of the pinhole inspection device.

FIG. 6 shows the configuration of the second embodiment of the pinhole inspection device.

In FIG. 6, numerals 11, 14, 15, and 16 identify the meter dial plate, X-Y table, illumination means, and imaging camera, respectively, which are configured in the same manner as in the first embodiment.

In FIG. 6, numeral 50 identifies the discrimination device. Discrimination device 50 comprises mask image/contour generation section 51, image under inspection generation section 20, and discrimination section 53.

i) Mask Image/Contour Generation Section 51

The mask image/contour generation section 51, in the same manner as in the above-described 1st embodiment, comprises analog/digital converter 22, selector switch 23, master image binary quantization section 24, and image inversion section 26, and is configured so as to generate a binarily quantized mask image c from mask image $b_1$, and further to generate an inverted binarily quantized master image (a mask image corresponding to the 1st mask image in the 1st embodiment) d from the binarily quantized mask image.

In addition, mask image/contour generation section 51 has a contour data generation section 54. Contour data generation section 54 generates contour data p for pattern area 12 from the binarily quantized master image c, and outputs this to the distance calculation section 55. While the method of generating contour data p will not be described in detail because it is publicly known in performing image processing, contour data p was generated by means of a borderline tracking algorithm which makes use of 8-neighborhood processing, which is widely used in image processing.

ii) Image Under Inspection Generation Section 20

The image under inspection generation section 20 has the same configuration as image under inspection generation section 20 of the first embodiment, and is configured generate a binarily quantized image under inspection after correcting the positioning skew of image under inspection $b_2$.

iii) Discrimination Section 53

The discrimination section 53 consists of mask section 56 and pinhole detection section 57.

Mask section 56 is configured so as to take the logical AND of the binarily quantized image under inspection e from image under inspection generation section 20 and the mask image d from mask image/contour generation section 51, setting pinhole parts 33 which exist in the background part 13 of the binarily quantized image under inspection to logic 1, and outputting this pinhole area data f to pinhole detection section 57. This pinhole data f has data contents similar to pinhole area data f1 in the 1st embodiment.

Pinhole detection section 57 consists of characteristic value measurement section 58, distance calculation section 55, discrimination threshold setting section 52, and discrimination section 59.

Characteristic value measurement section 58 is configured to use a geometric-type characteristic value measurement algorithm generally used in image processing to calculate the surface areas Si (i=1 to n) and centers of gravity (Xi, Yi) for each pinhole part i (corresponding in FIG. 8 to pinhole 1, pinhole 2, pinhole 3, . . . , pinhole n), based on pinhole area data f, and further to output this characteristic value data g to distance calculation section 55 and discrimination section 59.

Distance calculation section 55 calculates the center of gravity (Xi, Yi) for each pinhole i, based on the centers of gravity (Xi, Yi) for each pinhole indicated by characteristic value data g and on contour data p, and also calculates all the pixels j (j=1 to q) which form the contour of pattern area 12, according to the following equation (1).

$$Lj = \sqrt{\{(Xi - Xmj)^2 + (Yi - Ymj)^2\}} \quad (1)$$

(where (Xmj, Ymj) is the position data for pixel j)

In addition, the minimum distance Li of distances Lj of all the pixels j is determined by the following equation (2).

$$Li = \min \sqrt{\{(Xi - Xmj)^2 + (Yi - Ymj)^2\}} \quad (2)$$

(where j=1 to q)

This is taken as the pinhole to pattern distance Li, and distance data h is output to discrimination threshold setting section 52.

Further, another method of calculating the distances Lj which can be used when calculation speed is desired, although it suffers slightly in accuracy of distance Lj, is the following equation (3).

$$Lj = |Xi - Xmj| + |Yi - Ymj| \quad (3)$$

It is also possible to represent the contour of pattern area 12 with straight lines, using a line-segment approximations, the straight-line equation and pinhole i enter of gravity (Xi, Yi) being used to determine the distance Lj. This method also provides a means of increasing calculation speed.

Figure 7:
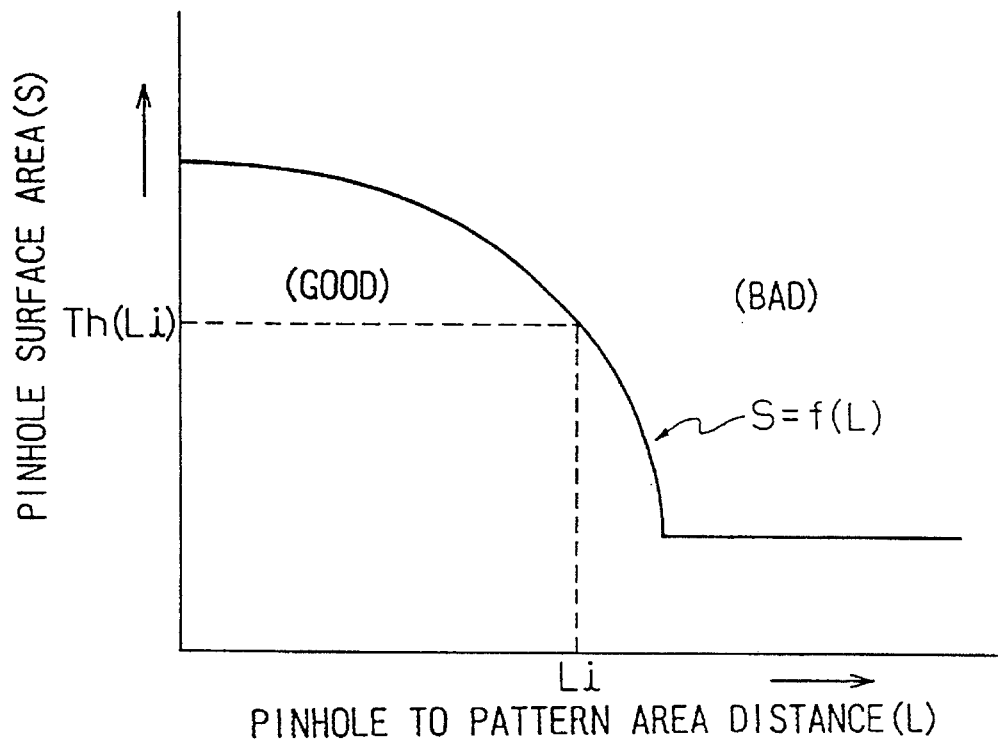
FIG. 7 is a graph explaining the discrimination surface area threshold.
Figure 8:
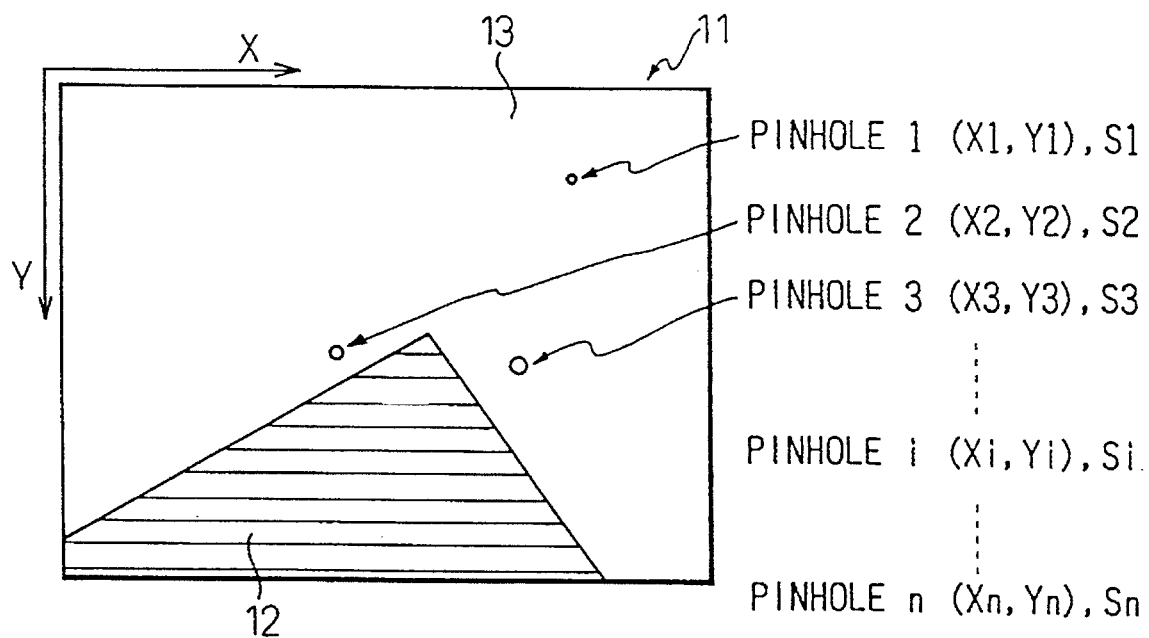
FIG. 8 illustrates the surface area and center of gravity of the pinholes.

Discrimination threshold setting section 52 is configured to set the pinhole surface area Th (Li) for use as the discrimination threshold for each pinhole, based on distance data h, with respect to the pinhole to pattern area distance indicated by said distance data h. Discrimination surface area threshold data k, which indicates the pinhole surface area Th(Li), is output to discrimination section 59. It is possible to determine pinhole surface area Th(Li) by, for example, setting up a function S=f(L) as shown in FIG. 7, in which the pinhole to pattern area distance L is a variable, and then substituting Li in L.

Discrimination section 59 is configured to perform, based on characteristic value data g and discrimination surface area threshold data k, a magnitude calculation, for each pinhole i, of the pinhole surface area Si indicated by characteristic value data g and the pinhole surface area Th(Li) indicated by the discrimination surface area threshold, so that if even one of the pinholes i the pinhole surface area Si is judged to be larger than the pinhole surface area Th(Li), the meter dial plate 11, which is the sample under inspection in the strict sense, is judged to be failed.

2. Operation

The following is a description of the operation of pinhole inspection device configured as described above. As described above, because the elements related o imaging camera 16, part of mask image/contour generation section 51 in discrimination device 50, image under inspection generation section 20, and mask section 56 in discrimination section 53 are configured the same way as corresponding elements in the 1st embodiment, the operation of these elements will not be covered. An explanation is given of an example of the operation of pinhole detection section 57 in discrimination section 53, making reference to the flowchart of FIG. 9.

The characteristic value measurement section 58 in pinhole detection section 57 measures for each pinhole i (i=1 to n), based on the pinhole section data g from mask section 56, the corresponding surface area Si and center of gravity (Xi, Yi), making use of a geometric-type characteristic value measurement algorithm generally used in image processing. This characteristic value data g is output to distance calculation section 55 and discrimination section 59 (step 100 shown in FIG. 9).

First, since i is set to 1 at step 101, distance calculation section 55 calculates the centers of gravity (Xi, Yi) for pinhole 1 of characteristic value data g and all of the distances Lj for all the pixels j (j=1 to q)which form the contour of pattern area 12, using above-noted equation (1), and further determine the minimum distance Li using above-noted equation (2), establishing this as the pinhole to pattern area distance Li, and outputs this distance data h to discrimination threshold setting section 52 (step 102).

Discrimination threshold setting section 52 substitutes Li into the variable in the function S=f(L) which has the pinhole to pattern area distance as a variable, and determines the pinhole surface area Th (Li) as the threshold value, while discrimination section 59 performs a magnitude comparison (at step 103) between pinhole 1 of the characteristic value data g and pinhole surface area S1.

If $S_1$ is smaller than Th(Li), steps 102 and 103 are then executed for pinhole 2, and if $S_2$ is smaller than Th(L2), this is done for pinhole 3, above processing being sequentially executed until Si is judged to be larger than Th(Li) (steps 104 and 105).

If Si is judged to be larger than TH(Li) before processing reaches the last pinhole n, discrimination section 59 judges that "the meter dial plate, which is the sample under test in the strict sense, is failed" (step 106).

If, on the other hand, all Si are judged to be smaller than Th(Li) up to the last pinhole n, discrimination section 59 judges that "meter dial plate 11 is passable" (step 107).

Figure 9:
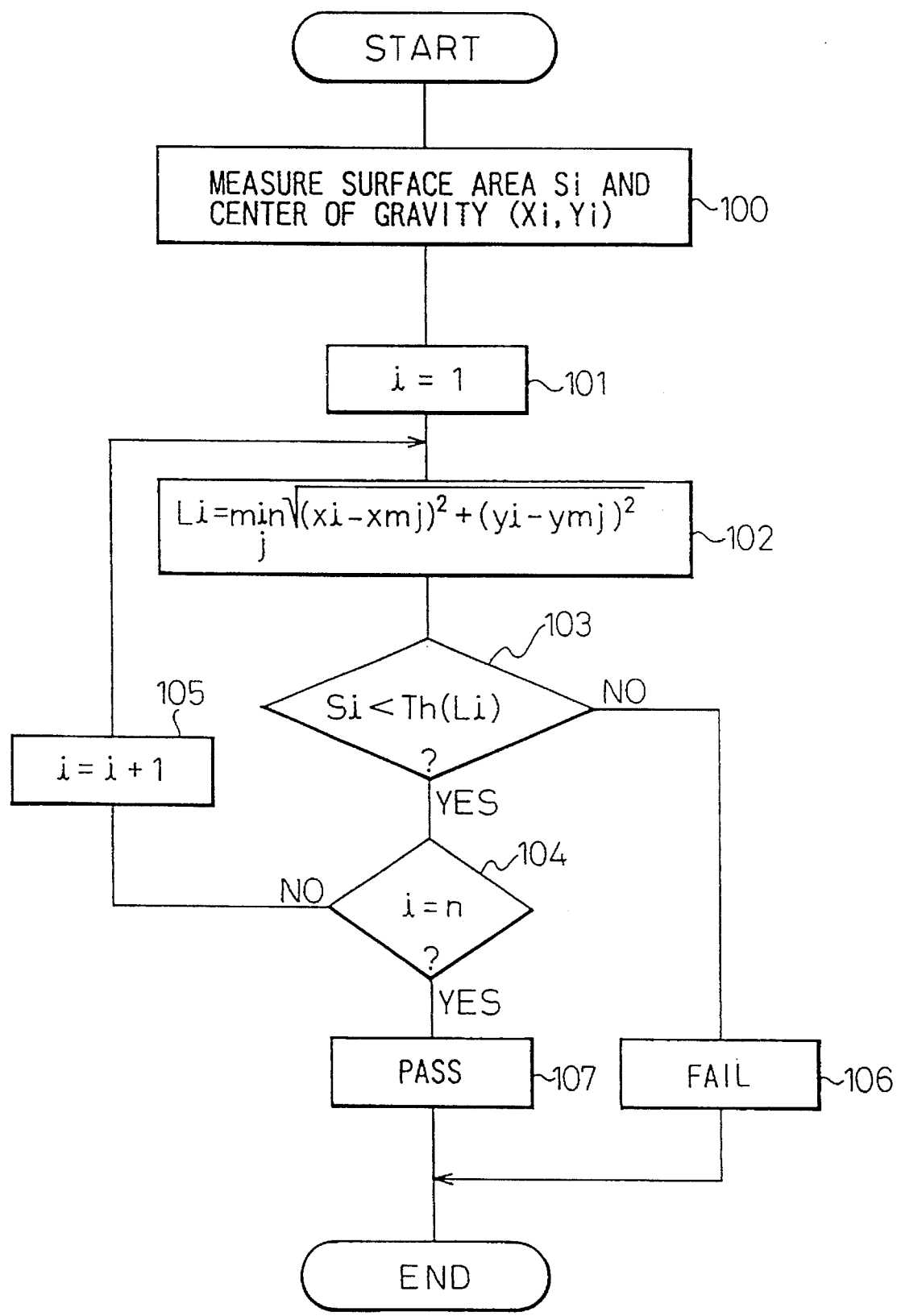
FIG. 9 is a flowchart explaining the operation of the pinhole detection section.

The flowchart shown in FIG. 9 is provided to make the explanation of the operation of pinhole detection section 57 easy to understand, and pinhole detection section 57 is not limited to implementation in the form of computer software, FIG. 9 not being intended to exclude implementation using a combination of existing hardware.

As described above, the discrimination device 50 of the 2nd implementation of the pinhole inspection device, comprises mask image/contour generation section 51 which, in addition to generating from the image signal a of a known good sample the master image $b_1$, which is then binarily quantized and inverted to form mask image d, also generates the contour of pattern area 12 of binarily quantized master image c, image under inspection generation section 20, which generates a binarily quantized image under inspection from the image signal a of the sample under inspection, and discrimination section 53, which takes the logical AND of the binarily quantized image under inspection e end the mask image d, calculates the surface area Si for each pinhole area i existing in background area 13, calculates the distance Li from each pinhole i to pattern area 12 based on the pattern area contour, sets the surface area Th(Li) as the discrimination threshold with respect to said calculated distance Li, performs a magnitude comparison of said discrimination surface area threshold Th(Li) with calculated surface area Si, and if calculated surface Si is larger than the discrimination surface area threshold Th(Si), judges said sample under inspection to be bad.

The discrimination surface area threshold used herein is established based on visual inspection criteria.

For this reason, using this embodiment of the pinhole inspection device, it is possible, in a similar manner as with the 1st embodiment, to perform a pass/fail discrimination which approximates a visual inspection.

I claim:

1. A device for inspecting a plate-shaped product having a pattern area through which inspection rays can pass and a background area, and for detecting and evaluating flaws in said background area, said flaws corresponding to portions of said background area which allow said inspection rays to pass therethrough, said device comprising:

(a) holding means for holding said product to be inspected;

(b) an inspection ray source providing said inspection rays to a first side of said product;

(c) an imaging camera arranged so as to obtain an image of a second side of said product illuminated by said inspection ray source, said image including a pattern portion corresponding to said pattern area and a background portion corresponding to said background area;

(d) masking means for masking said pattern portion of said image to prevent inspection rays that pass through said pattern area from appearing in a masked image of said product while permitting inspection rays that pass through said background area to appear as spots in said masked image, said spots in said masked image corresponding to said flaws in said background area of said product;

(e) means for detecting a size of each of said spots in said masked image and a distance of each of said spot from said pattern portion;

(f) means for defining thresholds corresponding to an allowable maximum limit of a size of each of said spots, said thresholds being defined such that a value of a threshold associated each spot decreases as said distance of that spot from said pattern portion increases; and (g) means for comparing said actual size of each of said spots to one of said thresholds to determine whether said size of said spot exceeds a maximum limit so as to cause said product to be rejected.

2. A device according to claim 1, wherein said threshold is defined by said defining means such that said value of said threshold decreases progressively in steps as said distance of said spot from said pattern portion increases.

3. A device according to claim 1, further comprising;

a plurality of additional masking means for masking regions of said background portion within a predetermined distance from said pattern portion to delete any of said spots corresponding to flaws in said regions of said background portion within said predetermined distance from said pattern portion so as to obtain images of said spots in said background portions outside said masked regions, wherein a size of said region masked by each of said plurality of additional masking means is varied, and wherein said threshold defining means comprises a plurality of threshold setters, wherein one threshold setter is associated with each of said additional masking means, each of said plurality of threshold setters providing a different value of said threshold based on a size of said region of said background masked by said additional masking means such that a value of said threshold provided by said threshold setter decreases as said size of said region being masked by said additional masking means increases.

4. A device according to claim 1, wherein said detecting means comprises:

means for calculating said actual size of each of said spots in said masked image; and means for calculating said distance of said each of said spots in said masked image from said pattern portion, and wherein said threshold defining means comprises:
means for storing a predetermined relationship between values of said distance of said spots from said pattern portion and values of said thresholds, such that a value of said threshold decreases as said distance of said spots from said pattern portion increases; and
means for calculating a value of said threshold from said calculated value of said distance of said spot from said pattern portion.

5. A device for inspecting a plate-shaped product having a pattern area through which inspection rays can pass and a background area, and for detecting and evaluating flaws in said background area, said flaws corresponding to portions of said background area which allow said inspection rays to pass therethrough, said device comprising:

(a) holding means for holding said product to be inspected;

(b) an inspection ray source for providing said inspection rays to one side of said product for illuminating said product held by said holding means;

(c) an imaging camera arranged so as to obtain an image of a second side said product illuminated by said inspection rays, said image of said product including a pattern portion corresponding to said pattern area and a background portion corresponding to said background area;

(d) masking means for masking a region of said image that includes both said pattern portion of said image of said product and a first portion of said background portion located within a predetermined distance from said pattern portions to prevent inspection rays that pass through said pattern portion and inspection rays that pass through said first portion of said background portion from appearing in a masked image of said product while permitting inspections rays that pass through said background portion outside said region to appear as spots in said masked image, said spots in said masked image corresponding to said flaws in said background area;

(e) means for defining thresholds corresponding to an allowable maximum limit of a size of said spots such that a value of said threshold decreases as said predetermined distance of said first portion from said pattern portions increases;

(f) means for detecting an actual size of said spots in said masked image of said product under inspection; and (g) means for comparing said actual size of said spots with said threshold to determine if a corresponding size of said spots exceeds said threshold causing said product to be rejected.

6. A device according to claim 5, wherein said masking means comprises:

means for obtaining an inverted binarily quantized image of a master product having no flaws therein as a first binarily quantized master image;

means for magnifying said first binarily quantized master image by various different magnification ratios to obtain a plurality of second binarily quantized master images each having a different magnification;

means for obtaining a binarily quantized image of said product; and means for taking a logical multiplication between said binarily quantized image of said product and each of said first and said second binarily quantized master images to obtain said masked image of said product.

7. A device according to claim 5, wherein said masking means comprises:

an analog-to-digital converter for obtaining a binarily quantized image of said image produced by said imaging camera;

a switch having a first position where a binarily quantized image of a master product having no flaws is obtained if said master product is being inspected, and a second position where a binarily quantized image of said product is obtained if said product is being inspected;

means, connected to said analog-to-digital converter when said switch is in said first position, for inverting said binarily quantized image of said master product to obtain a first binarily quantized masked image;

means for magnifying said first binarily quantized image at different magnification ratios to obtain a plurality of second binarily quantized masked images;

means, connected to said analog-to-digital converter when said switch is in said second position, for obtaining a binarily quantized image of said product; and means for taking a logical multiplication between said binarily quantized image of said product and each of said first and said second binarily quantized masked images to obtain said masked image of said product.

8. A device according to claim 7, further comprising means for correcting a positional difference between an image of said product in said holding means with respect to an image of said master product.

9. A device for inspecting a plate-shaped product having a pattern area through which said inspection rays can pass and a background area, and for detecting and evaluating flaws in said background area, said flaws corresponding to portions of said background area which allow said inspection rays to pass therethrough, said device comprising:

(a) holding means for holding said product to be inspected;

(b) an inspection ray source for providing said inspection ray to a first side of said product held by said holding means;

(c) an imaging camera arranged so as to obtain an image of a second side of said product illuminated by said inspection rays, said image of said product including a pattern portion corresponding to said pattern area and a background portion corresponding to said background area;

(d) masking means for masking a region of said image, said region including both said pattern portion of said image and a first portion of said background portion located within a predetermined distance from said pattern portions to prevent inspection rays that pass through said pattern portions and inspection rays that pass through said first portion from appearing in a masked image of said product while permitting inspections rays that pass through said background areas outside said region to appear as spots in said masked image, said spots in said masked image corresponding to said flaws in said background area of said product;

(e) distance measuring means for measuring a distance of each of said spots in said masked image from said pattern portion of said product;

(f) size measuring means for measuring a size of each of said spots in said background area outside said region;

(g) means for setting a threshold corresponding to an allowable maximum limit of a size of said spots such that said value of threshold decreases as said distance of said spots from said pattern portion increases; and (h) means for comparing said size of each of said spots with said threshold to determine if said size of said spots exceeds said threshold causing said product to be rejected.

10. A device according to claim 9, wherein said distance measuring means comprises:

means for determining a periphery of said pattern portion in said image of said product;

means for calculating distances of each of said spots from different locations on said periphery of said pattern portion; and means for determining a minimum value of said distances obtained by said calculating means, said minimum value of said distances being used as said distance by said threshold setting means.

11. A device according to claim 9, wherein said masking means comprises:

means for obtaining an inverted binarily quantized image of a master product having no flaws therein as an inverted binarily quantized master image;

means for binarily quantizing said image of said product under inspection to obtain a binarily quantized detected image; and means for taking a logical multiplication between said inverted binarily quantized master image and said binarily quantized detected image to obtain said masked image of said product.

12. A device according to claim 9, wherein said masking means comprises:

an analog-to-digital converter for obtaining a binarily quantized image of said image produced by said imaging camera;

a switch having a first position where a binarily quantized image of a master product having no flaws is obtained if said master product is being inspected, and a second position where a binarily quantized image of said product is obtained if said product is being inspected;

means, connected to said analog-to-digital converter when said switch is in said first position, for inverting said binarily quantized image of said master product to obtain a binarily quantized masked image;

means, connected to said analog-to-digital converter when said switch is in said second position, for binarily quantizing said image of said product; and means for taking a logical multiplication between said binarily quantized image of said product and said binarily quantized master image to obtain said masked image of said product.

13. A device according to claim 12, further comprising means for correcting a positional difference of said image of said product in said holding means with respect to said image of said master product.

14. A method for inspecting a plate-shaped product, which comprises a pattern area through which inspection rays can pass and a background area, and for detecting and evaluating flaws in said background area, said flaws corresponding to portions of said background area which allow said inspection rays to pass therethrough, said method comprising the steps of:

(a) providing a product to be inspected;

(b) illuminating said product with said inspection rays;

(c) obtaining an image of said product illuminated by said inspection rays, said image including a pattern portion corresponding to said pattern area and a background portion corresponding to said background area;

(d) masking said pattern portion of said image so as to obtain a masked image of said product from which any of said flaws occurring in said background area of said product are detected;

(e) detecting spots in said background portion of said masked image, said spots corresponding to said flaws in said background area of said product and determining a size of each of said spots;

(f) detecting a spacing of said spots from said pattern portion in said masked image;

(g) defining threshold values corresponding to an allowable maximum limit of a size of each of said spots, said threshold values being defined such that a value of said threshold decreases as said spacing of one of said spots from said pattern portion increases; and (h) comparing said size of each of said spots to a corresponding threshold value to determine whether a size of each of said spots exceeds a maximum limit so as to cause said product to be rejected.

15. A method of inspecting a plate-shaped product having a pattern area through which inspection rays can pass and a background area, and for detecting and evaluating flaws in said background area, said flaws corresponding to portions of said background area which allow said inspection rays to pass therethrough, said method comprising the steps of:

(a) providing said product to be inspected;

(b) providing said inspection rays to a first side of said product for illuminating said product;

(c) obtaining an image of said product illuminated by said inspection rays, said image of said product including a pattern portion corresponding to said pattern area and a background portion corresponding to said background area;

(d) masking a region of said image of said product that includes said pattern portions and a first portion of said background portion located within a predetermined distance from said pattern portions to prevent inspection rays that pass through said pattern portions and inspection rays that pass through said first portion from appearing in a masked image of said product while permitting inspections rays that pass through said background portion outside said region to appear as spots in said masked image, said spots corresponding to said flaws in said background area of said product;

(e) defining different values of a threshold corresponding to an allowable maximum limit of a size of said spots in said masked image such that a value of said threshold decreases as said predetermined distance increases;

(f) detecting an actual size of said spots in said masked image of said product under inspection; and (g) comparing said actual size of said spots with said threshold to determine if said size of said spots exceeds said threshold causing said product to be rejected.

16. A method of inspecting a plate-shaped product having a pattern area through which said inspection rays can pass and a background area, and for detecting and evaluating flaws in said background area, said flaws corresponding to portions of said background area which allow said inspection rays to pass therethrough, said method comprising the steps of:

(a) providing said product to be inspected;

(b) providing said inspection ray to a first side of said product;

(c) obtaining an image of said product illuminated by said inspection rays, said image of said product including a pattern portion corresponding to said pattern area and a background portion corresponding to said background area;

(d) masking a region of said image of said product that includes said pattern portion said a first portion of said background portion located within a predetermined distance from said pattern portions to prevent inspection rays that pass through said pattern portions and inspection rays that pass through said first portion from appearing in a masked image of said product while permitting inspections rays that pass through said background portion outside said region to appear as spots in said masked image, said spots corresponding to said flaws in said background area of said product;

(e) measuring a distance of each of said spots in said background portion outside said region from said pattern portion;

(f) measuring a size of each of said spots in said background portion outside said region;

(g) setting a threshold corresponding to an allowable maximum limit of a size of said spots such that a value of said threshold decreases as said distance of said spots from said pattern portion increases; and (h) comparing said size of each of said spots with said threshold to determine if said size of said spots exceeds said threshold causing said product to be rejected.

* * * * *